United States Patent [19]

Akasaki et al.

[11] Patent Number: 5,041,665

[45] Date of Patent: Aug. 20, 1991

[54] PROCESS FOR PREPARING SQUARYLIUM COMPOUNDS

[75] Inventors: Yutaka Akasaki; Akihiko Tokida; Kaoru Torikoshi; Akira Imai; Hidemi Suto, all of Kanagawa, Japan

[73] Assignee: Fuji Xerox Co., Ltd., Tokyo, Japan

[21] Appl. No.: 278,397

[22] Filed: Dec. 1, 1988

[30] Foreign Application Priority Data

Dec. 4, 1987 [JP]  Japan ................... 62-305857
Dec. 4, 1987 [JP]  Japan ................... 62-305858

[51] Int. Cl.$^5$ .................... C07C 215/68; C07C 215/70
[52] U.S. Cl. ........................ 564/307; 564/92; 564/185
[58] Field of Search ............... 564/305, 306, 307, 185, 564/92

[56] References Cited

U.S. PATENT DOCUMENTS

| | | | |
|---|---|---|---|
| 4,524,219 | 6/1985 | Law | 564/307 |
| 4,524,220 | 6/1985 | Law | 564/307 |
| 4,525,592 | 6/1985 | Law et al. | 564/307 |
| 4,624,904 | 11/1986 | Kazmaier et al. | 430/59 |
| 4,700,001 | 10/1987 | Tanaka et al. | 564/307 |
| 4,707,427 | 11/1987 | Tanaka et al. | 564/307 X |

*Primary Examiner*—Richard L. Raymond
*Attorney, Agent, or Firm*—Finnegan, Henderson, Farabow, Garrett and Dunner

[57] ABSTRACT

A process for preparing a squarylium compound useful as a photoconductive material for an electrophotographic photoreceptor, in which process comprises reacting an arylhydroxycyclobutenedione salt or a hydroxycyclobutenedione derivative with an aniline derivative is disclosed. The process comprises dropwise adding a solution of the arylhydroxycyclobutenedione salt or hydroxycyclobutenedione derivative in a solvent, to an alcohol solution of the aniline derivative in an alcohol solvent. An electrophotographic photoreceptor produced by using the thus obtained squarylium compound exhibits and sensitivity, satisfactory chargeability, low dark decay, low residual potential, and excellent stability after repeated use.

11 Claims, No Drawings

PROCESS FOR PREPARING SQUARYLIUM COMPOUNDS

FIELD OF THE INVENTION

This invention relates to an improved process for producing a squarylium compound.

BACKGROUND OF THE INVENTION

A number of organic or inorganic substances have been recommended as photoconductive materials for electrophotograhic photoreceptors and the like. Known organic photoconductive materials include bisazo pigments, trisazo pigments, phthalocyanine pigments, cyanine compounds, and pyrylium compounds. It has recently been reported that certain kinds of squarylium compounds exhibit excellent photoconductive characteristics.

Known squarylium compounds include symmetrical comopunds in which the right and left of the 4-membered ring thereof are symmetrical with each other and asymmetrical compounds in which the right and left of the 4-membered ring thereof are asymmetrical. These compounds are inclusively represented by formula (III):

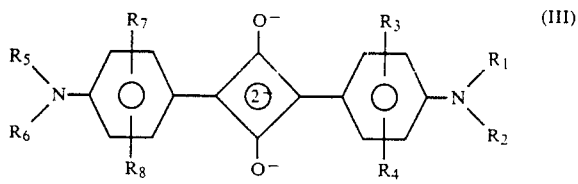

wherein $R_1$, $R_2$, $R_5$, and $R_6$ each represents a substituted or unsubstituted alkyl group, a substituted or unsubstituted phenyl group, or a substituted or unsubstituted benzyl group; and $R_3$, $R_4$, $R_7$, and $R_8$ each represents a hydrogen atom, a substituted or unsubstituted alkyl group, a halogen atom, a hydroxyl group, a carboxyl group, a carbonamido group substituted with a substituted or unsubstituted alkyl group or a substituted or unsubstituted phenyl group, or a sulfonamido group substituted with a substituted or unsubstituted alkyl group or a substituted or unsubstituted phenyl group.

In general, the symmetrical squarylium compounds are synthesized by reacting squarylic acid with the corresponding aniline derivative in an alcohol.

On the other hand, the asymmetrical squarylium compounds are synthesized through the following reactions. Squarylic acid is chlorinated with a chlorinating agent, e.g., thionyl chloride, and the chlorinated compound is reacted with an aniline derivative to form a chlorocyclobutenedione derivative. The resulting compound is hydrolyzed to obtain a hydroxycyclobutene derivative, which is then reacted with an aniline derivative different from that used above to synthesize an asymmetrical squarylium compound.

Improved processes for synthesizing squarylium compounds which have been proposed in the past include a process comprising reacting squarylic acid with a compound selected from the group consisting of an aromatic aniline, a phenol, and a phenolsquarylium compound as disclosed in JP-A-60-174750 (the term "JP-A" as used herein means an "unexamined published Japanese patent application"), a process comprising reacting a half ester of squarylic acid with an aniline derivative in the presence of an acid catalyst as disclosed in JP-A-60-202849, a process comprising reacting squarylic acid with an aromatic aniline in the presence of an aliphatic amine as disclosed in JP-A-60-208361, and a process comprising reacting squarylic acid, an aromatic aniline, and fluoroaniline as disclosed in JP-A-61-87647.

These conventionally proposed processes are characterized in that the reaction conditions are set so as to reduce impurities or, in the alternative, various impurities are intentionally introduced into the synthesis system, in order to improve the electrophotographic characteristics of the resulting squarylium compound for use as a photoconductive material of electrophotographic photoreceptors. However, none of the above-cited references has elucidated what factors influence the electrophotographic characteristics of the produced squarylium compound. Therefore, only a slight alteration in the reaction conditions would result in variation of the electrophotographic characteristics of the resulting squarylium compound when used as a photoconductive material of electrophotographic photoreceptors. In such situations, it has been difficult to continually and reproducibly prepare a stable squarylium compound which is suited for use in electrophotographic photoreceptors processing satisfactory electrophotographic characteristics.

SUMMARY OF THE INVENTION

It is an object of this invention to provide a process for preparing a squarylium compound suitable for producing an electrophotographic photoreceptor exhibiting high sensitivity, satisfactory chargeability, low dark decay, low residual potential, and excellent stability with repeated use.

As a result of extensive and intensive investigations, it has now been found that a hydroxycyclobutene derivative, produced as an intermediate, is an impurity in the resulting squarylium compound and influences the electrophotographic characteristics of the electrophotographic photoreceptor produced by using the squarylium compound, such as chargeability, dark decay, stability with repeated use, and the like. In particular, in the synthesis of asymmetrical squarylium compounds starting with the hydroxybutene derivative, it was confirmed by liquid chromatographic analysis that the hydroxybutene derivative is incorporated into the produced crystals due to its low solubility in a reaction solvent system. It is therefore a further object of this invention to provide a high purity squarylium compound.

Additional objects and advantages of the invention will be set forth in the description which follows, and in part will be apparent from the description, or may be learned by practice of the invention. The objects and advantages of the invention may be realized and obtained by means of the instrumentalities and combinations particularly pointed out in the appended claims.

To achieve the foregoing objects, and in accordance with the purposes of the invention as embodied and broadly described hereinthere is provided a process for preparing a squarylium compound represented by formula (III):

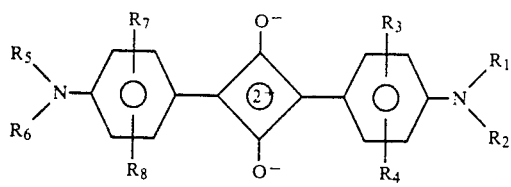

wherein $R_1$, $R_2$, $R_3$, $R_4$, $R_5$, $R_6$, $R_7$, and $R_8$ are as defined above, which comprises dropwise adding a solution of an arylhydroxycyclobutenedione salt represented by formula (I-1):

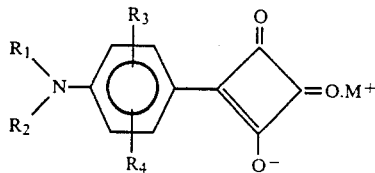

wherein $R_1$, $R_2$, $R_3$, and $R_4$ are as defined above: and $M^+$ represents an alkali metal ion, a tetraalkylammonium ion, a trialkylammonium ion, a substituted or unsubstituted pyridinium in, or a substituted or unsubstituted quinolinium ion, preferably a trialkylammonium ion, or a hydroxycyclobutendione derivative represented by formula (I-2):

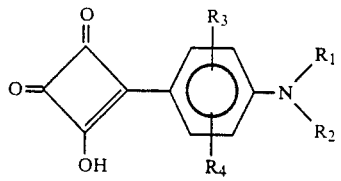

wherein $R_1$, $R_2$, $R_3$, $R_4$ are as defined above, in a solvent, to a solution of an aniline derivative represented by formula (II):

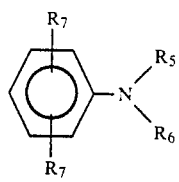

wherein $R_5$, $R_6$, $R_7$, and $R_8$ are as defined above, in an alcohol solvent, to effect reaction.

According to the process of this invention, there is provided a high purity squarylium compound. The resulting squarylium compound is suitable for producing an electrophotographic photoreceptor having high sensitivity, satisfactory chargeability, low dark decay, low residual potential, and excellent stability to repeated use.

DETAILED DESCRIPTION OF THE INVENTION

Reference will now be made in detail to the presently preferred embodiment of the invention.

Squarylium compounds of this invention include symmetrical compounds in which the right and left of the 4-membered ring thereof are symmetrical with each other and asymmetrical compounds in which the right and left of the 4-membered ring thereof are asymmetrical. These compounds are inclusively represented by formula (III):

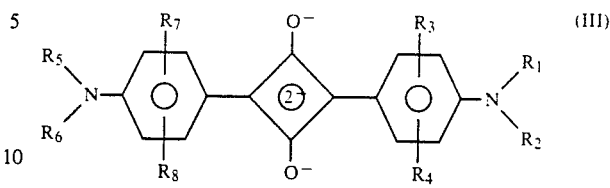

wherein $R_1$, $R_2$, $R_5$, and $R_6$ each represents a substituted or unsubstituted alkyl group (preferably having from 1 to 20 carbon atoms), a substituted or unsubstituted phenyl group (preferably having from 6 to 30 carbon atoms), or a substituted or unsubstituted benzyl group (preferably having from 7 to 30 carbon atoms); and $R_3$, $R_4$, $R_7$, and $R_8$ each represents a hydrogen atom, a substituted or unsubstituted aklyl group, a halogen atom, a hydroxyl group, a carboxyl group, a carbonamido group substituted with a substituted or unsubstituted alkyl group or a substituted or unsubstituted phenyl group, or a sulfonamido group substituted with a substituted or unsubstituted alkyl group or a substituted or unsubstituted phenyl group.

Specific examples of substituents to be substituted on an alkyl group, a phenyl group, or a benzyl group include an alkyl group (preferably having from 1 to 20 carbon atoms), an alkoxy group (preferably having from 1 to 20 carbon atoms) and a halogen atom (for example, F, Cl, Br and I).

In cases of using, as a starting material, an arylhydroxycyclobutenedione salt represented by formula (I-1), the reaction is carried out by dropwise addition of a solution of the starting material in a solvent to an alcohol solution comprising an aniline derivative represented by formula (II) and an alcohol solvent.

The arylhydroxycyclobutenedione salt of formula (I-1) can be obtained by treating an arylhydroxycyclobutenedione represented by formula (IV) as described in U.S. Pat. No. 4,624,904:

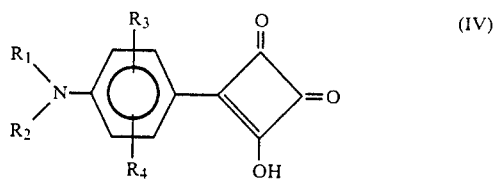

wherein $R_1$, $R_2$, $R_3$, and $R_4$ are as defined above, with a base. Preferably, $R_3$ and $R_4$ each represents —F, —Cl or —OH.

Typical examples of the arylhydroxycyclobutenedione of formula (IV) are shown below.

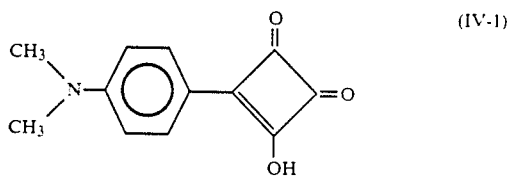

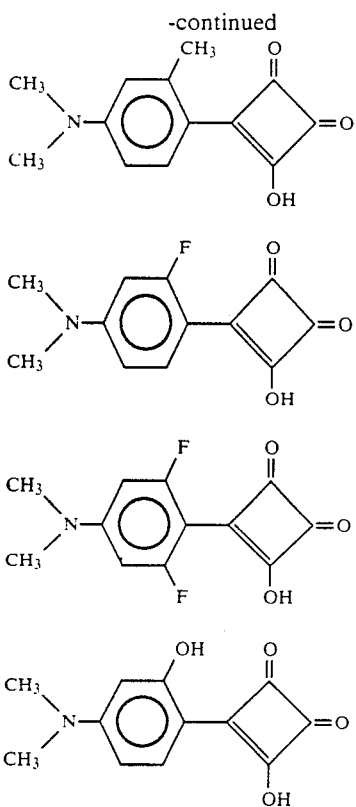

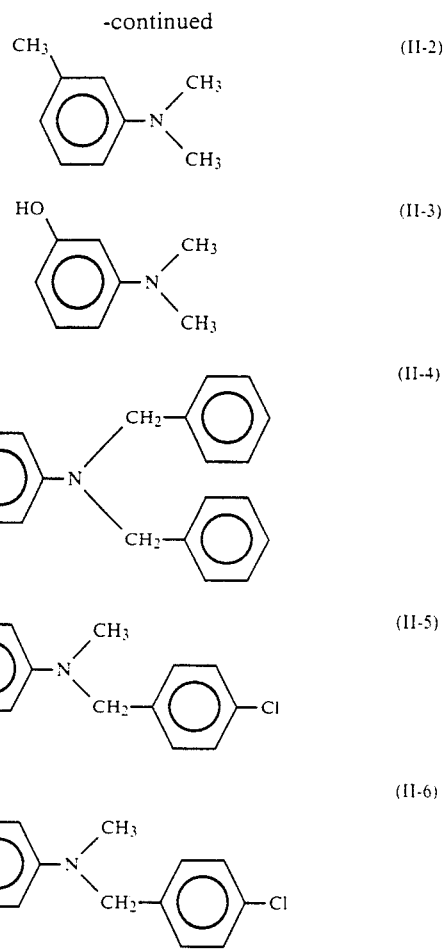

Among these, the compounds of formulae (IV-1) and (IV-3) are preferred.

The base which can be used includes alkali metal hydroxides, secondary aliphatic amines, tertiary aliphatic amines (e.g., triethylamine and tri(n-buty)amine), pyridines (e.g., pyridine and methylpyridine), and quinolines (e.g., quinoline and methylquinoline).

Of the arylhydroxycyclobutenedione salts of formula (I-1), those wherein M+ is a trialkylammonium ion are preferred.

The solvent for dissolving the arylhydroxycyclobutenedione of formula (I-1) has a boiling point of from 90° to 110° C. under the condition of a reduced pressure of several hundreds mmHg or less (preferably from 5 mmHg to 50 mmHg) and contains little water, the solvent preferably includes aliphatic alcohols having from 4 to 8 carbon atoms (e.g., 1-butanol, 1-heptanol, and 1-octanol) and mixed solvents comprising these aliphatic alcohols and aromatic hydrocarbons (e.g., benzene and toluene). The solvent may be the same as or different from a reaction solvent to be used in the reaction with the aniline derivative of formula (II). One or more of other inert solvents may also be used as long as they do not interfere with the reaction.

Specific examples of the aniline derivative represented by formula (II) are shown below.

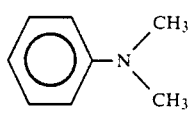

Among these, the derivatives of formulae (II-3), (II-5) and (II-6), in which $R_7$ or $R_8$ represents an —OH group or in which an N-substituent represents an alkylalyl group or an alkyl-benzyl group are preferred.

In carrying out the reaction, the aniline derivative is dissolved in an alcohol as a reaction solvent to form an alcohol solution. It is preferable that the alcohol solution of the aniline derivative further contains an acidic substance. The acidic substance to be added may be organic or inorganic and preferably includes those having a pKa value of less than 5, such as sulfuric acid, toluenesulfonic acid, trichloroacetic acid, monochloroacetic acid, phosphoric acid, oxalic acid, tartaric acid, benzoic acid, acetic acid, etc., with sulfuric acid being preferred. In a reaction system showing relatively high reactivity, oxalic acid is preferably used. The acidic substance is generally used in an amount at least equivalent, preferably from 1.1 to 3 equivalents, based on the arylhydroxycyclobutenedione salt.

The alcohol reaction solvent to be used preferably includes an aliphatic alcohol having from 4 to 8 carbon atoms (e.g., 1-butanol, 1-heptanol, and 1-octanol) and a mixed solvent of such an aliphatic alcohol and an aromatic hydrocarbon (e.g. benzene and toluene).

In the present invention, the solution of the arylhydroxycyclobutenedione salt of formula (I-1) is preferably added dropwise to an alcoholic solution comprising the aniline derivative and a reaction solvent selected from an alcohol solvent and a mixed solvent thereof.

The aniline derivative is preferably used in an amount of from 1 to 3 equivalents based on the amount of the arylhydroxycyclobutenedione salt at the completion of dropwise-addition.

The reaction proceeds sufficiently simply by heating the reactants in the reaction solvent. If desired, water produced during the reaction may be removed by using a Dean Stark trap (i.e., a device for removing water which is produced by the reaction) or a dehydrating agent or by heating under reduced pressure. The reaction temperature preferably ranges from about 60° C. to about 140° C. and more preferably ranges from about 90° C. to about 120° C., and the reaction time is from about 1 to about 50 hours.

The rate of dropwise addition of the arylhydroxycyclobutenedione salt solution is preferably as low as possible within a practically acceptable range. Actually, the solution is added dropwise to the reaction solvent while throughly stirring over a period of from 10 minutes to 10 hours, preferably from 1 to 5 hours. The rate of addition of the arylhydroxycyclobutenedione salt ranges preferably from 0.01 to 10 mmol/min and more preferably from 0,01 to 1 mmol/min.

It is preferable to maintain the acidity of the reaction system constant. This can be achieved by incorporating into the system a salt or base corresponding to the above-described acidic substance to have the system buffered. The buffering system to be used includes an oxalic acid/lithium oxalate system, an oxalic acid/triethylamine system, a phosphoric acid/tributylamine system, an acetic acid/sodium acetate system, an acetic acid/triethanolamine system, etc.

On the other hand, when the hydroxycyclobutenedione derivative represented by formula (I-2) is used as a starting compound, the compound of formula (I-2) is dissolved in a polar solvent, and the solution is added dropwise to an alcohol solution of the aniline derivative represented by formula (II) to effect reaction.

The polar solvent for dissolving the hydroxycyclobutenedione derivative preferably include diemthyl sulfoxide and dimethylfomamide.

The alcohol solvent for dissolving the aniline derivative preferably includes an aliphatic alcohol having from 4 to 8 carbon atoms, e.g., n-butyl alcohol and n-heptyl alcohol. A mixed solvent comprising the aliphatic alcohol and, as an azeotropic solvent, an aromatic hydrocarbon, e.g., benzene and toluene, may also be used.

The reaction should be carried out by dropwise addition of the solution of the hydroxycyclobutenedione derivative in a polar solvent to an alcohol solution of the aniline derivative.

The aniline derivative is preferably used in an amount of from 1 to 3 equivalents based on the amount of the hydroxycyclobutenedione derivative at the completion of the dropwise-addition. The reaction proceeds sufficiently simply by heating the reaction system in the solvent. If desired, water produced during the reaction may be removed by using a Dean Stark trap or a dehydrating agent or by heating the reaction system under reduced pressure to remove the produced water. The reaction temperature preferably ranges from about 60° C. to about 140° C. and more preferably ranges from about 90° C. to about 120° C. and the reaction time is from about 1 to about 50 hours. When an aliphatic alcohol having a boiling point of 140° C. or more is used, the reaction is preferably conducted under reduced pressure of from 5 to 200 Torr.

The rate of dropwise addition of the arylhydroxycyclobutenedione derivative solution is preferably as low as possible within a practically acceptable range. Actually, the rate of addition of the hydrocyclobutenedione derivative preferably ranges from 0.01 to 10 mmol/min and more preferably from 0.01 to 1 mmol/min.

Specific examples of the squarylium compounds represented by formula (III) which can be prepared by the process of this invention are shown below.

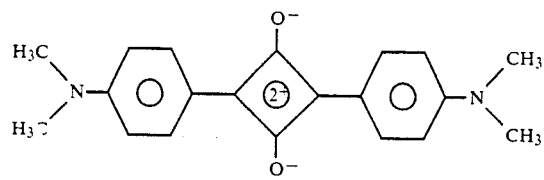

III-1

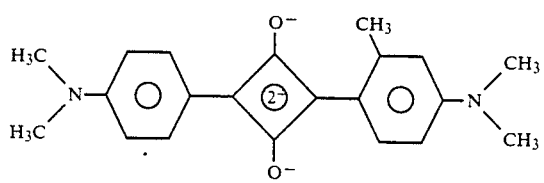

III-2

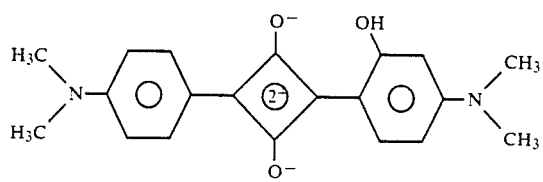

III-3

-continued
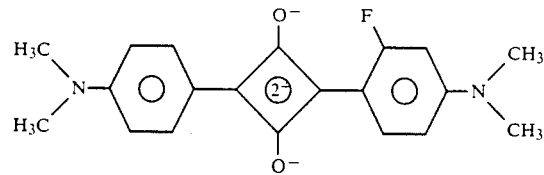
III-4
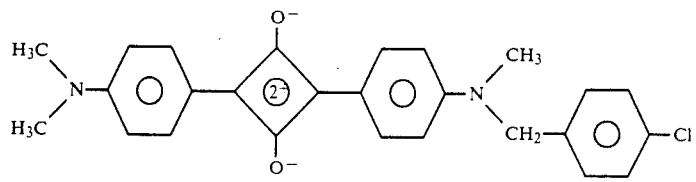
III-5
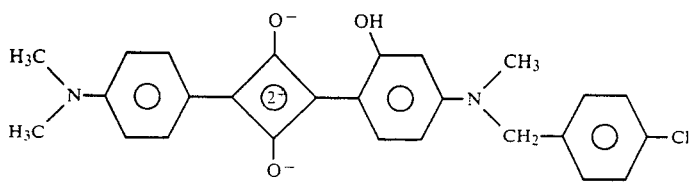
III-6
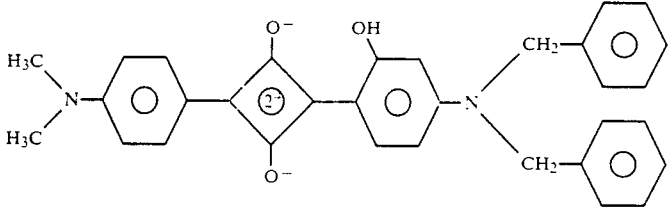
III-7
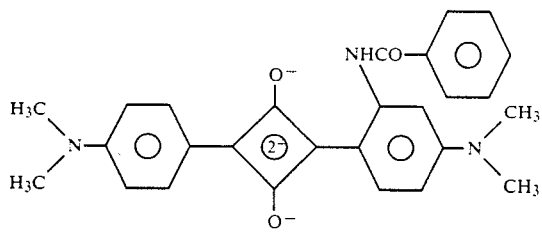
III-8
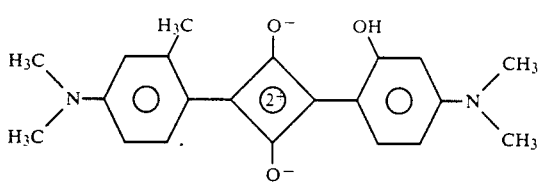
III-9
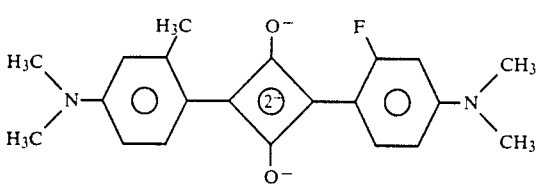
III-10
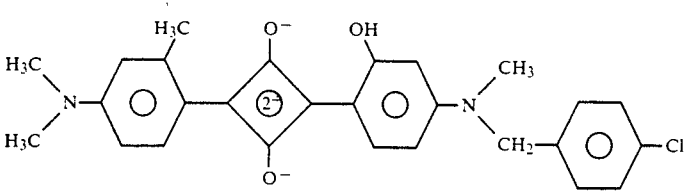
III-11

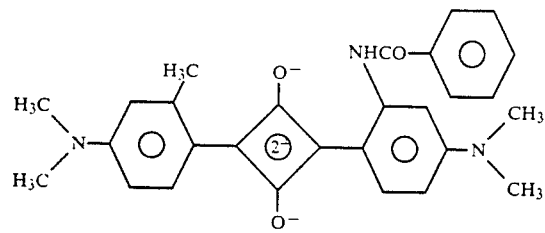
III-12
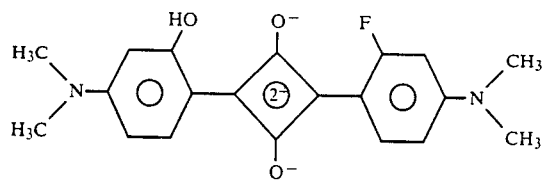
III-13
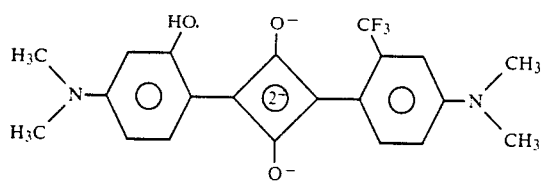
III-14
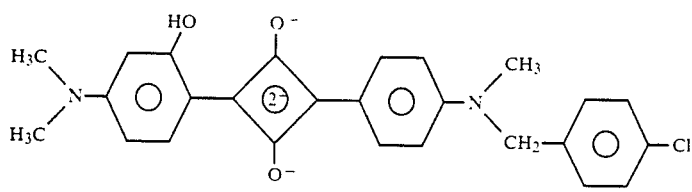
III-15
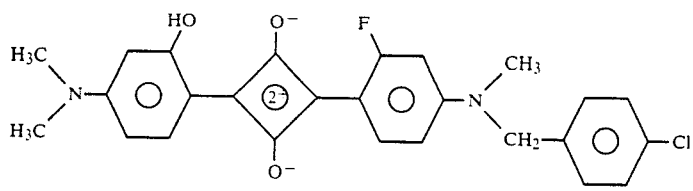
III-16
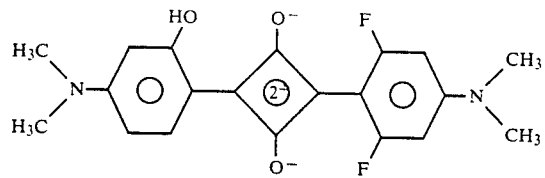
III-17
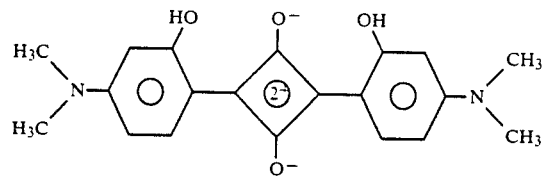
III-18
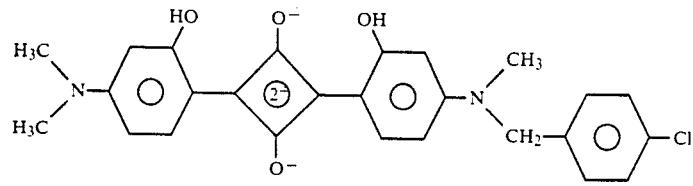
III-19

III-20
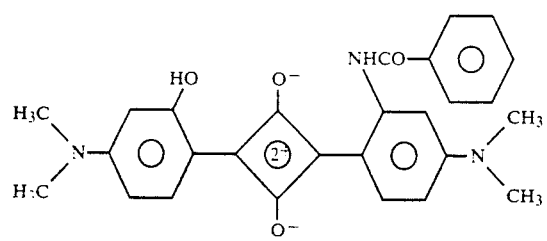
III-21
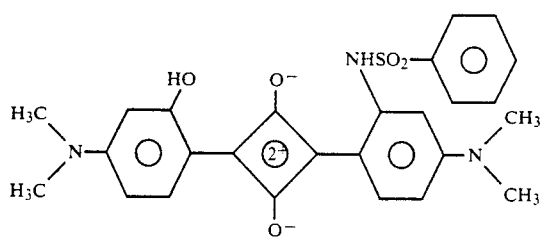
III-22
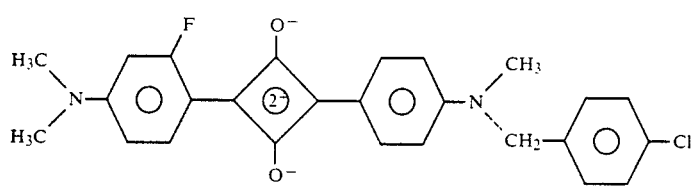
III-23
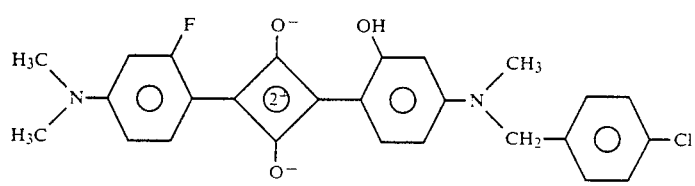
III-24
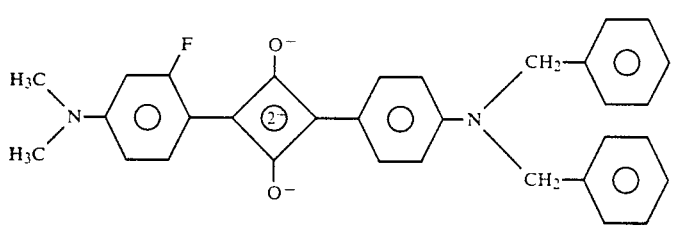
III-25
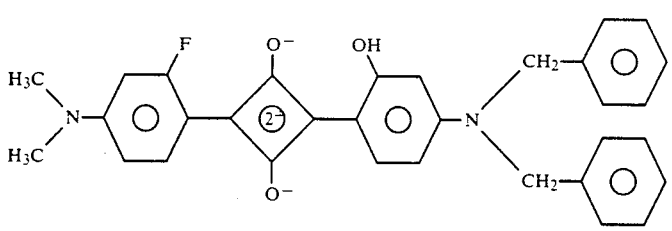
III-26
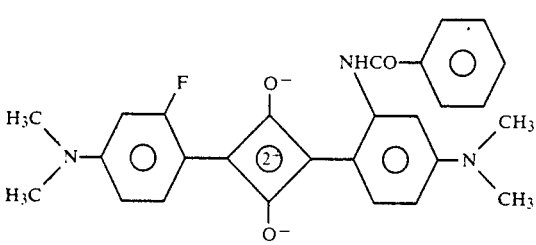

-continued
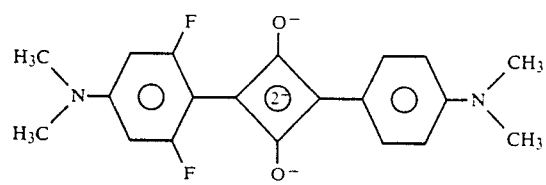
III-27
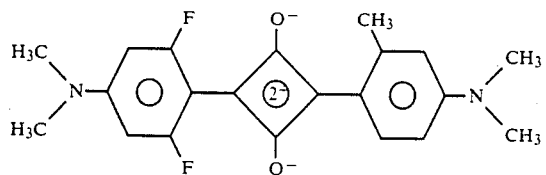
III-28
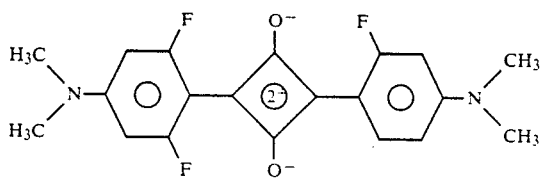
III-29
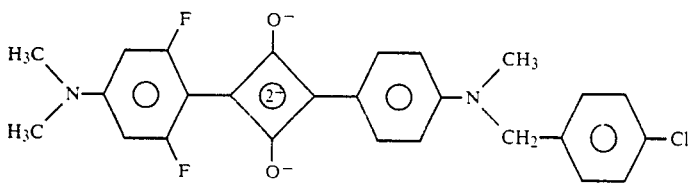
III-30
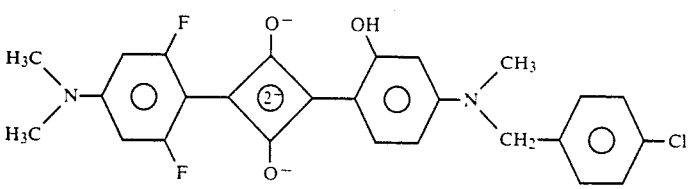
III-31
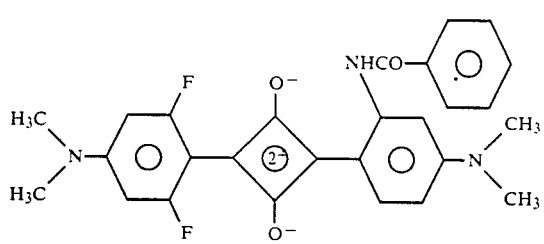
III-32
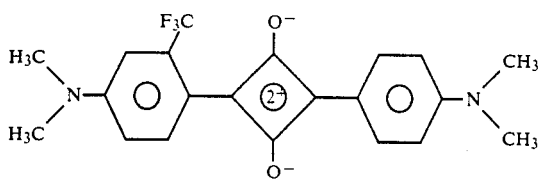
III-33
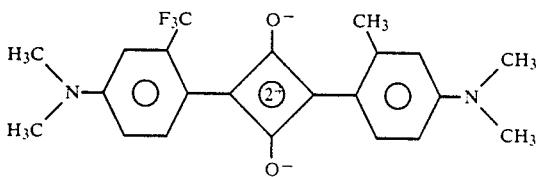
III-34

-continued
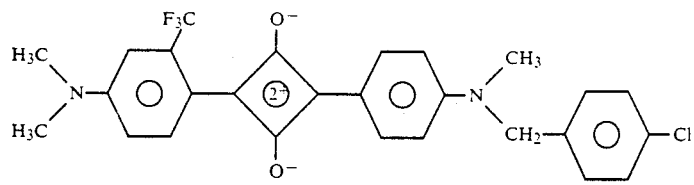 III-35
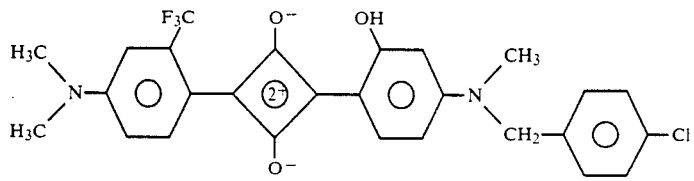 III-36
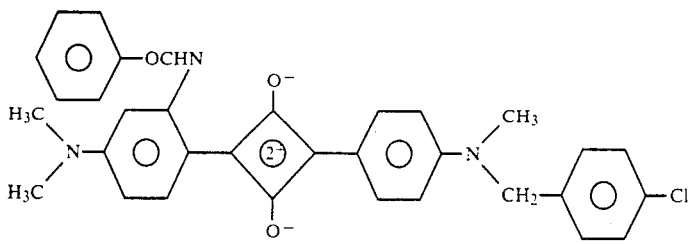 III-37
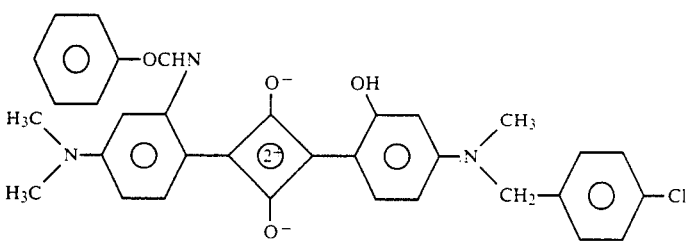 III-38
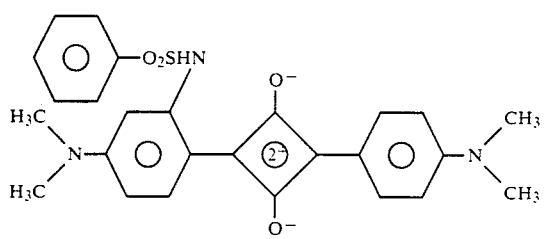 III-39
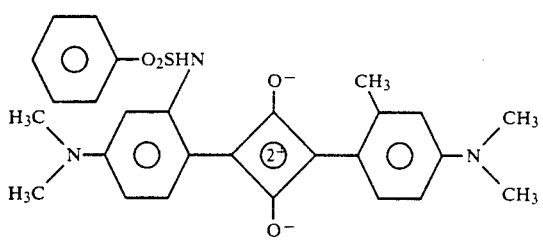 III-40
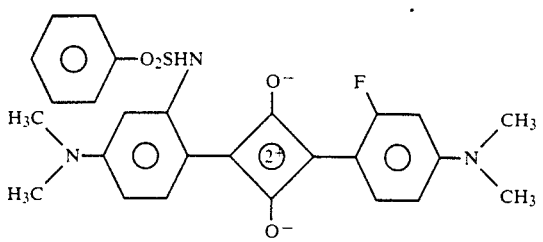 III-41

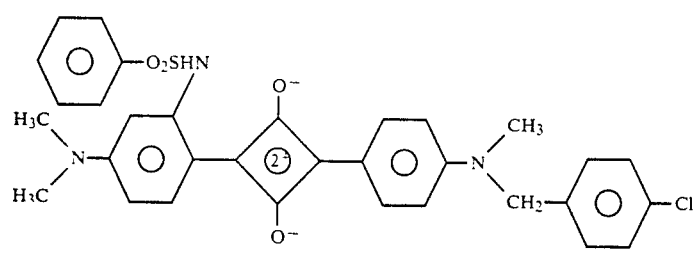
III-42
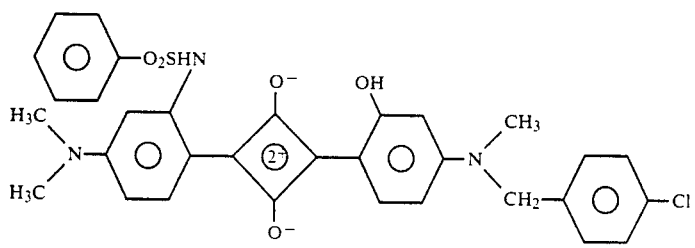
III-43
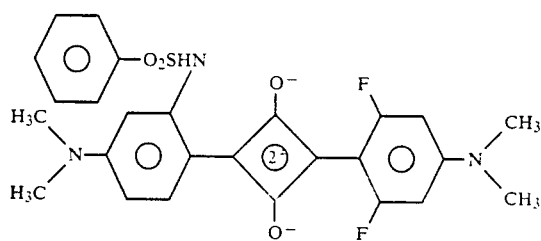
III-44
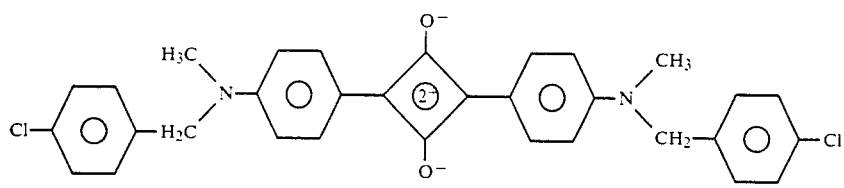
III-45
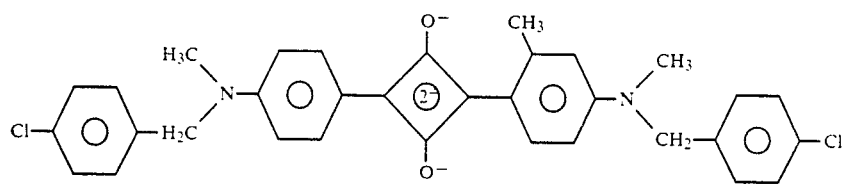
III-46
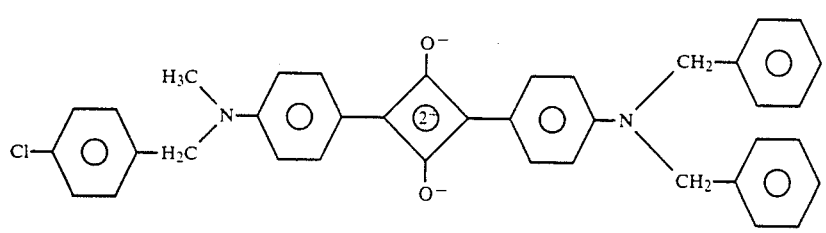
III-47
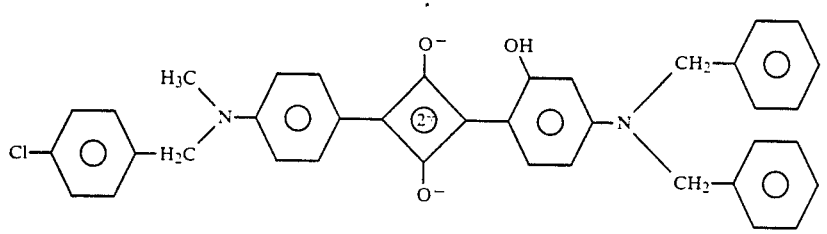
III-48

-continued
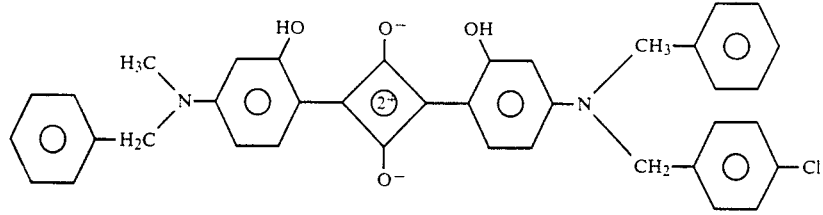
III-49
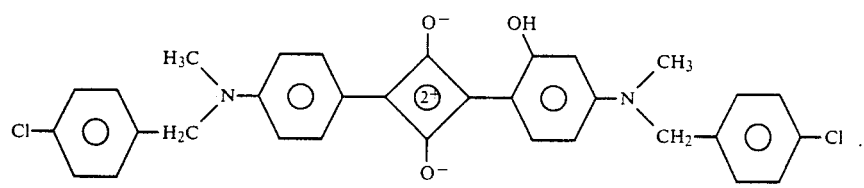
III-50
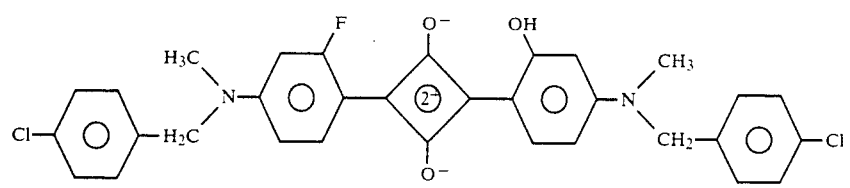
III-51
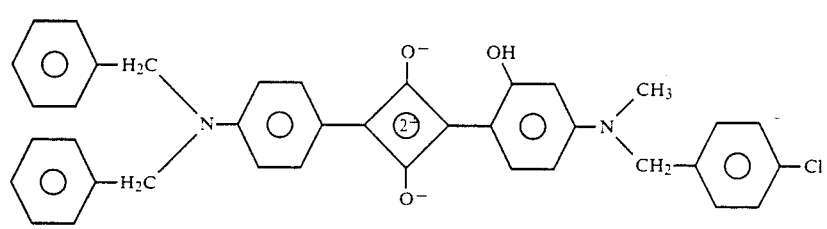
III-52
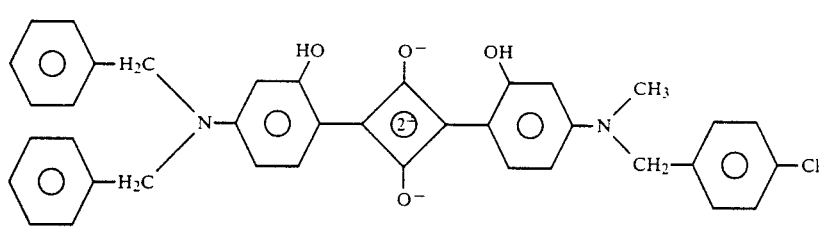
III-53
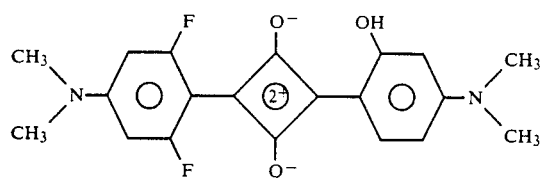
III-54
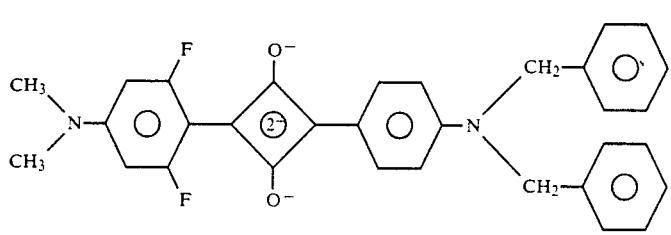
III-55

III-56

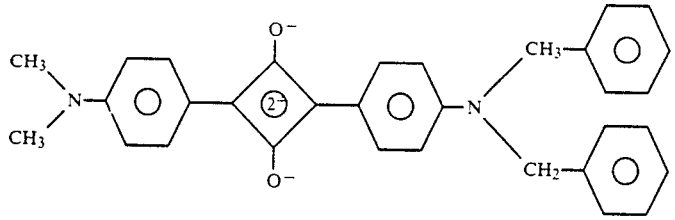

According to the process of the present invention, squarylium compounds of high purity can be prepared. The resulting squarylium compounds are suitable as photoconductive materials for electrophotographic photoreceptors. When applied to an electrophotographic photoreceptor having separated functions in which a photosensitive layer has a laminate structure comprising a charge generating layer and a charge transporting layer, the squarylium compound can be incorporated into the charge generating layer as a charge generating agent to thereby provide an electrophotographic photoreceptor exhibiting high sensitivity, satisfactory chargeability, low dark decay, low residual potential, and excellent stability to repeat use.

The present invention is now illustrated in greater detail by referring to the following Examples and Comparative Examples, but it should be understood that the present invention is not deemed to be limited thereto. In these examples, all the parts are by weight unless otherwise indicated.

EXAMPLE 1

1) Synthesis of Triethylammonium 4-(4'-Dimethylaminophenyl)-1-Cylobutene-1,2-Dione-3-Oleate In 50 ml of methanol was dispersed 2.2 g (10 mmol) of 3-hydroxy-4-(4'-dimethylaminophenyl)-1-cyclobutene-1,2-dione (Compound IV-1), and 2 ml (14 mmol) of triethylamine was added thereto, followed by dissolving completely. The solvent was removed under reduced pressure, and the resulting solid was washed with hexane and dried to obtain 3.2 g (yield: 98%) of the entitled compound having the following formula as an orange colored powder having a melting point of 83° to 85° C.

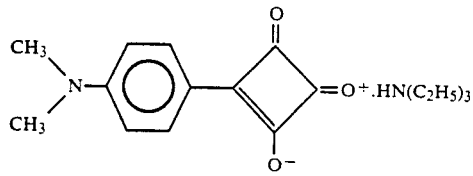

Elementary Analysis:
Calcd. (%): C 67.90; H 8.23; N 8.80
Found (%): C 67.72; H 8.11; N 8.84

2) Synthesis of Compound III-3

In 50 ml of 1-butanol were dissolved 1.37 g (10 mmol) of N,N-dimethyl-m-aminophenol (Compound II-3) and 0.9 g (10 mmol) of oxalic acid. Separately, 2.55 g (8 mmol) of the triethylammonium 4-(4'-dimethylaminophenyl)-1-cyclobutene-1,2-dione-3-oleate prepared in synthesis (1) above was dissolved in 20 ml of 1-butanol, and the solution was added dropwise to the above prepared solution while stirring at reflux over a period of about 2 hours. After the dropwise addition, the mixture was further refluxed for about 2 hours. The thus precipitated deep blue crystals were collected by filtration, washed, and dried to obtain 2.40 g (yield: 89%) of Compound III-3 having a melting point of 292° C. (with decomposition).

3) Production of Electrophotographic Photoreceptor

To 1 part of Compound III-3 as syntehsized in (2) above were added 1 part of a polyvinyl butyral resin ("BXL" produced by Sekisui Chemical Co., Ltd.) and 40 parts of cyclohexanone, and the mixture was mixed and pulverized in a ball mill for 4 hours. The resulting dispersion was coated on a polyester film on which aluminum had been deposited ("METALUMY" produced by Toray Inds., Inc.) by means of a bar coater and dried to form a 0.2 μm thick charge generating layer.

A uniform solution consisting of 1 part of N,N'-diphenyl-N,N'-bis(3-methylphenyl)-1-[1,1'-biphenyl]-4,4'-diamine, 1 part of a polycarbonate resin ("PANLITE" produced by Teijin Limited), and 10 parts of tetrahydrofuran was coated on the charge generating layer and dried to form a 15 μm thick electron transporting layer to thereby obtain an electrophotographic photoreceptor.

4) Evaluation of Electrophotographic Photoreceptor

The resulting electrophotographic photoreceptor was negatively charged to −6 kV by corona discharge using means of an electrostatic copying paper testing apparatus ("Electrostatic Paper Analyzer SP-428" manufactured by Kawaguchi Denki Co., Ltd.) and allowed to stand in the dark for 2 seconds. Then, the photoreceptor was exposed to light emitted from a tungsten lamp at a surface illumination of 5 lux for 10 seconds.

The surface potential immediately after the charging ($V_0$,) the potential after 2 seconds standing in the dark (VDDP), the exposure required for reducing the surface potential to half of VDDP ($E_{\frac{1}{2}}$), and the surface potential after 10 seconds exposure to light of 5 lux (VRP) were measured. The same measurements were repeated 20 times. The results obtained are shown in the following Table 1.

COMPARATIVE EXAMPLE 1

To 50 ml of 1-butanol were added 1.23 g (9 mmol) of N,N-dimethyl-m-aminophenol and 1.73 g (8 mmol) of 3-hydroxy-4-(4'-dimethylaminophenyl)-1-cyclobutene-1,2-dione (Compound IV-1), and the mixture was refluxed for 4 hours with stirring. After allowing the mixture to cool, the precipitated crystals were collected by filtration, washed, and dried to obtain 2.50 g (yield: 93%) of Compound III-3.

An electrophotographic photoreceptor was produced by using the resulting compound in the same manner as in Example 1-3) and evaluated in the same manner as in Example 1-4). The results obtained are shown in Table 1.

EXAMPLE 2

In 100 ml of a 2/1 (by volume) mixed solvent of 1-butanol and toluene was dissolved 2.73 g (10 mmol) of N,N-dibenzylaniline (Compound II-4), and 0.5 ml of concentrated sulfuric acid was added thereto. Separately, a solution of 2.55 g (8 mmol) of triethylammonium 4-(4'-dimethylaminophenyl)-1-cyclobutene-1,2-dione-3-oleate as prepared in Example 1- 1) was dissolved in 20 ml of 1-butanol, and the solution was added dropwise to the above prepared solution in a reaction vessel equipped with a Dean Stark trap while stirring at reflux over a period of about 2 hours. After the dropwise additon, the refluxing was continued for an additional period of 20 hours, followed by allowing the mixture to cool to room temperature. The precipitated crystals were filtered, washed, and dried to obtain 1.25 g (yield: 33%) of Compound III-56 having a melting point of 250° C. (with decomposition).

An electrophotographic photoreceptor was produced in the same manner as in Example 1-3), except for replacing Compound III-3 with Compound III-56, and evaluated in the same manner as in Example 1-4). The results obtained are shown in Table 1.

COMPARATIVE EXAMPLE 2

To 100 ml of a 2/1 (by volume) mixed solvent of 1-butanol and toluene were added 1.23 g (9 mmol) of N,N-dimethyl-m-aminophenol, 1.73 g of 3-hydroxy-4-(4'-dimethylaminophenyl)-1-cyclobutene-1,2-dione, and 2.73 g (10 ml) of N,N-dibenzylaniline, and the mixture was stirred at reflux for 30 hours while removing produced water by a Deam Stark trap. After allowing the mixture to cool, precipitated crystals were collected by filtration, washed, and dried to obtain 0.98 g (yield: 26%) of Compound III-56.

An electrophotographic photoreceptor was produced by using the above obtained Compound III-56 and evaluated in the same manner as in Example 1-3) and 4), respectively. The results obtained are shown in Table 1.

EXAMPLE 3

To 1.88 g (8 mmol) of 3-hydroxy-4-(4'-dimethylamino-2'-fluorophenyl)-1-cyclobutene-1,2-dione (Compound IV-3) were added 20 ml of 1-butanol and 1.2 ml (9 mmol) of triethylamine to prepare a solution. The resulting solution was added dropwise to a solution of 1.37 g (10 mmol) of N,N-dimethyl-m-aminophenol (Compound II-3), 2.2 g (24 mmol) of oxalic acid, and 1.1 ml (8 mmol) of triethylamine in 50 ml of 1-butanol while stirring at reflux over a period of about 2 hours. After the addition, the refluxing was further continued for 5 hours. The precipitated bluish green crystals were collected by filtration, washed, and dried to obtain 1.69 g (yield: 60%) of Compound III-13 having a melting point of 290° C. (with decomposition).

An electrophotographic photoreceptor was produced in the same manner as in Example 1-3), except for using the thus prepared Compound III-13 in place of Compound III-3, and evaluated in the same manner as in Example 1-4). The results obtained are shown in Table 1.

COMPARATIVE EXAMPLE 3

Compound III-13 was synthesized in the same manner as in Comparative Example 1 (yield: 1.61 g; 57%).

An electrophotographic photoreceptor was produced in the same manner as in Example 1-3), except for using the thus prepared Compound III-13, and evaluated in the same manner as in Example 1-4). The results obtained are shown in Table 1.

EXAMPLE 4

To 1.88 g (8 mmol) of 3-hydroxy-4-(4'-dimethylamino-2'-fluorophenyl)-1-cyclobutene-1,2-dione (Compound IV-3) were added 20 ml of 1-butanol and 1.2 ml (9 mmol) of triethylamine to prepare a solution.

Separately, 2.32 g (10 mmol) of N-methyl-N-(p-chlorobenzyl)-aniline was dissolved in 100 ml of a 2/1 (by volume) mixed solvent of 1-butanol and toluene, and 0.5 ml of concentrated sulfuric acid was added thereto. To the resulting solution was added dropwise the above prepared solution while stirring at reflux in a reaction vessel equipped with a Dean Stark trap over a period of about 2 hours. After the addition, the refluxing was further continued for 17 hours. The precipitated crystals were collected by filtration, washed, and dried to obtain 1.60 g (yield: 45%) of Compound III-22 having a melting point of 250° C. (with decomposition).

An electrophotographic photoreceptor was produced in the same manner as in Example 1-3), except for using the above obtained Compound III-22, and evaluated in the same manner as in Example 1-4). The results obtained are shown in Table 1.

COMPARATIVE EXAMPLE 4

Compound III-22 was synthesized in the same manner as in Comparative Example 2 (yield: 2.64 g; 73%).

An electrophotographic photoreceptor was produced in the same manner as in Example 1- 3), except for using the above synthesized Compound III-22, and evaluated in the same manner as in Example 1-4). The results obtained are shown in Table 1.

EXAMPLE 5

To 1.88 g (8 mmol) of 3-hydroxy-4-(4'-dimethylamino-2'-fluorophenyl)-1-cyclobutene-1,2-dione (Compound IV-3) were added 25 m( of a 2/1 (by volume) mixture of 1-butanol and toluene and 2.4 ml (10 mmol) of tri(m-butyl)amine to prepare a solution.

Then, the resulting solution was added dropwise to a solution of 2.48 g (10 mmol) of N-methyl-N-(p-chlorobenzyl)-m-aminophenol (Compound II-6), 2.2 g (24 mmol) of oxalic acid, and 1.9 ml (8 mmol) of tri(n-butyl)amine in 100 m( of a 2/1 (by volume) mixed solvent of 1-butanol and toluene while stirring at reflux in a reaction vessel equipped with a Dean Stark trap over a period of about 2 hours. After the dropwise addition, the refluxing was further continued for an additional period of 4 hours. The precipitated crystals were collected by filtration, washed, and dried to obtain 2.96 g (80 %) of Compound III-23 having a melting point of 268° C. (with decomposition).

An electrophotographic photoreceptor was produced in the same manner as in Example 1-3), except for using the above prepared Compound III-23, and evaluated in the same manner as in Example 1-4). The results obtained are shown in Table 1.

COMPARATIVE EXAMPLE 5

Compound III-23 was synthesized in the same manner as in Comparative Example 2 (yield: 2.53 g; 68%).

An electrophotographic photoreceptor was produced in the same manner as in Example 1–3), except for using the above prepared Compound III-23. The results of evaluations are shown in Table 1.

TABLE 1

| Example No. | Time of Measurement | $V_0$ (V) | VDDP (V) | $E_{\frac{1}{2}}$ (lux · sec) | VRP (V) |
|---|---|---|---|---|---|
| Example | | | | | |
| 1 | 1 | 740 | 700 | 1.1 | 0 |
|   | 20 | 735 | 695 | 1.1 | 0 |
| 2 | 1 | 800 | 780 | 4.0 | 5 |
|   | 20 | 790 | 770 | 4.0 | 5 |
| 3 | 1 | 795 | 755 | 1.0 | 0 |
|   | 20 | 780 | 740 | 1.0 | 0 |
| 4 | 1 | 850 | 820 | 1.0 | 0 |
|   | 20 | 845 | 815 | 1.0 | 0 |
| 5 | 1 | 780 | 755 | 0.9 | 0 |
|   | 20 | 780 | 750 | 0.9 | 0 |
| Comparative Example | | | | | |
| 1 | 1 | 430 | 330 | 1.1 | 15 |
|   | 20 | 390 | 260 | 1.0 | 15 |
| 2 | 1 | 700 | 750 | 3.8 | 25 |
|   | 20 | 680 | 630 | 3.7 | 30 |
| 3 | 1 | 540 | 435 | 1.1 | 15 |
|   | 20 | 460 | 360 | 0.9 | 15 |
| 4 | 1 | 795 | 750 | 1.1 | 0 |
|   | 20 | 750 | 700 | 1.0 | 0 |
| 5 | 1 | 630 | 570 | 1.3 | 10 |
|   | 20 | 600 | 525 | 1.2 | 5 |

EXAMPLE 6

1) Synthesis of Compound III-3

In 180 ml of n-butyl alcohol was added 1.26 g of 3-dimehtylaminophenol, followed by heating with stirring. To the resulting solution was added dropwise a solution of 2.00 g of 3-hydroxy-4-(4'-dimethylaminophenyl)-3-cyclobutene-1,2-dione in 40 ml of dimethyl sulfoxide over a period of about 1.5 hours while heating. Thereafter, the resulting mixture was heat-refluxed for 18 hours. After completion of the reaction, the formed precipitate was collected by filtration and washed with methanol and dimethyl ether to obtain 2.93 g of Compound III-3 having a melting point of 317° C. (with decomposition).

Elementary Analysis for $C_{20}H_{20}N_2O_3$:
Calcd. (%): C 71.41; H 5.99; N 8.33
Found (%): C 71.47; H 5.81; N 8.29

Liquid chromatography of the product revealed that the product contained 41 ppm of 3-hydroxy-4-(4'-dimethylaminophenyl)-3-cyclobutene-1,2-dione.

2) Production of Electrophotographic Photoreceptor

To 1 part of Compound III-3 synthesized in 1) above were added 1 part of a polyvinyl butyral resin ("BXL" produced by Sekisui Chemical Co., Ltd.) and 40 parts of cyclohexanone, and the mixture was mixed and pulverized in a ball mill for 4 hours. The resulting dispersion was coated on a polyester film on which aluminum had been deposited ("METALUMY" produced by Toray Inds., Inc.) by means of a bar coater and dried to form a 0.2 μm thick charge generating layer.

A uniform solution consisting of 1 part of N,N'-diphenyl-N,N'-bis(3-methylphenyl)-1-[1,1'-biphenyl]-4,4'-diamine, 1 part of a polycarbonate resin ("PANLITE" produced by Teijin Limited), and 10 parts of tetrahydrofuran was coated on the charge generating layer and dried to form a 15 μm thick electron transporting layer to thereby obtain an electrophotographic photoreceptor.

3) Evaluation of Electrophotographic Photoreceptor

The resulting electrophotographic photoreceptor was negatively charged to −6 kV by corona discharge by means of an electrostatic copying paper testing apparatus ("Electrostatic Paper Analyzer SP-528" manufactured by Kawaguchi Denki Co., Ltd.) and allowed to stand in the dark for 2 seconds. Then, the photoreceptor was exposed to light emitted from a tungsten lamp at a surface illumination of 5 lux for 10 seconds.

The surface potential immediately after the charging ($V_0$), the potential after 2 seconds standing in the dark (VDDP), the exposure required for reducing the surface potential to half of VDDP ($E_{\frac{1}{2}}$), and the surface potential after 10 seconds exposure to light of 5 lux (VRP) were measured. The same measurements were repeated 20 times. The results obtained are shown in the following Table 2.

EXAMPLE 7

To 210 ml of n-butyl alcohol was added 4.38 g of 3-dimethylaminophenol, followed by stirring with heating. To the resulting solution was added dropwise a solution of 2.50 g of 3-hydroxy-4-(4'-dimethylamino-2'-fluorophenyl)-3-cyclobutene-1,2-dione in 20 ml of dimethylsulfoxide over a period of about 1.5 hours while heating. Thereafter, the mixture was heat-refluxed for 14 hours. After completion of the reaction, the precipitate was filtered and washed with methanol and dimethyl ether to obtain 2.73 g of Compound III-13 having a melting point of 314° C. (with decomposition).

Elementary Analysis for $C_{20}H_{19}N_2O_3F$:
Calcd. (%): C 67.79; H 5.40; N 7.93
Found (%): C 67.79; H 5.40; N 7.87

Liquid chromatography of the product revealed that the content of 3-hydroxy-4-(4'-dimethylamino-2'-fluorophenyl)-3-cyclobutene-1,2-dione was 434 ppm.

An electrophotographic photoreceptor was produced in the same manner as in Example 6, except for using the above prepared Compound III-13. The results of evaluations are shown in Table 2.

COMPARATIVE EXAMPLE 6

In 180 ml of n-butyl alcohol were added 1.26 g of 3-dimethylaminophenol and 2.00 g of 3-hydroxy-4-(4'-dimethylaminophenyl)-3-cyclobutene-1,2-dione, and the mixture was allowed to react by heat-refluxing for 20 hours. After completion of the reaction, the precipitate was collected by filtration and washed with methanol and dimethyl ether to obtain 3.01 g of Compound III having a melting point of 316° C. (with decomposition).

Elementary Analysis for $C_{20}H_{20}N_2O_3$:
Calcd. (%): C 71.41; H 5.99; N 8.33
Found (%): C 71.37; H 5.80; N 8.28

Liquid chromatography of the product revealed that the content of 3-hydroxy-4-(4'-dimethylaminophenyl)-3-cyclobutene-1,2-dione was 13200 ppm.

An electrophotographic photoreceptor was produced in the same manner as in Example 6, except for using the above prepared Compound III. The results of evaluations are shown in Table 2.

COMPARATIVE EXAMPLE 7

To 210 ml of n-butyl alcohol were added 4.38 g of 3-dimethylaminophenol and 2.50 g of 3-hydroxy-4-(4'-dimethylamino-2'-fluorophenyl)-3-cyclobutene-1,2-dione, and the mixture was heat-refluxed for 20 hours. After completion of the reaction, the precipitate was collected by filtration and washed with methanol and dimethyl ether to obtain 3.03 g of Compound III-13 having a melting point of 298° C. (with decomposition).

Elementary Analysis for $C_{20}H_{19}N_2O_3F$:
Calcd. (%): C 67.79; H 5.40; N 7.93
Found (%): C 67.72; H 5.54; N 7.73

Liquid chromatography of the product revealed that the content of 3-hydroxy-4-(4'-dimethylamino-2'-fluorophenyl)-3-cyclobutene-1,2-dione was 11300 ppm.

An electrophotographic photoreceptor was produced in the same manner as in Example 6, except for using the above prepared Compound III-13. The results of evaluations are shown in Table 2.

TABLE 2

| Example No. | Time of Measurement | $V_0$ (V) | VDDP (V) | $E_{\frac{1}{2}}$ (lux · sec) | VRP (V) |
|---|---|---|---|---|---|
| Example | | | | | |
| 6 | 1 | 640 | 560 | 0.8 | 5 |
| | 20 | 635 | 555 | 0.9 | 5 |
| 7 | 1 | 720 | 680 | 0.8 | 10 |
| | 20 | 720 | 670 | 0.9 | 10 |
| Comparative Example | | | | | |
| 6 | 1 | 440 | 370 | 1.0 | 20 |
| | 20 | 420 | 350 | 1.1 | 25 |
| 7 | 1 | 540 | 460 | 1.0 | 20 |
| | 20 | 480 | 380 | 1.0 | 20 |

As described above, the squarylium compounds prepared by the process according to the present invention are excellent for use as photoconductive materials in electrophotographic photoreceptors. That is, the electrophotographic photoreceptors obtained by using the squarylium compounds of the present invention exhibit high sensitivity, satisfactory chargeability, low dark decay, low residual potential, and excellent stability after repeated use.

While the invention has been described in detail and with reference to specific embodiments thereof, it will be apparent to one skilled in the art that various changes and modifications can be made therein without departing from the spirit and scope thereof.

What is claimed is:

1. A process for preparing a squarylium compound represented by formula (III):

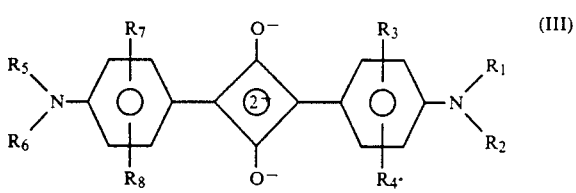

wherein $R_1$, $R_2$, $R_5$, and $R_6$ each represents a substituted or unsubstituted alkyl group, a substituted or unsubstituted phenyl group, or a substituted or unsubstituted benzyl group; and $R_3$, $R_4$, $R_7$, and $R_8$ each represents a hydrogen atom, a substituted or unsubstituted alkyl group, a halogen atom, a hydroxyl group, a carboxyl group, a carbonamido group substituted with a substituted or unsubstituted alkyl group or a substituted or unsubstituted phenyl group, or a sulfonamido group substituted with a substituted or unsubstituted alkyl group or a substituted or unsubstituted phenyl group, in which process comprises dropwise adding a solution of an arylhydroxycyclobutenedione salt represented by formula (I-1):

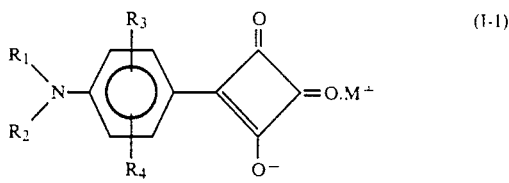

wherein $R_1$, $R_2$, $R_3$, and $R_4$ are as defined above; and $M^+$ represents an alkali metal ion, a tetraalkylammonium ion, a trialkylammonium ion, a substituted or unsubstituted pyridinium ion, or a substituted or unsubstituted quinolinium ion, or a hydroxycyclobutendione derivative represented by formula (I-2):

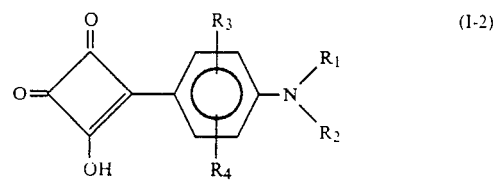

wherein $R_1$, $R_2$, $R_3$, $R_4$ are as defined above, in a solvent, to an alcohol solution of an aniline derivative represented by formula (II):

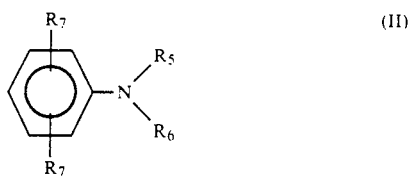

wherein $R_5$, $R_6$, $R_7$, and $R_8$ are as defined above, in an alcohol solvent, to effect reaction.

2. The process as claimed in claim 1, wherein said solvent for the solution of the arylhydroxycyclobutenedione salt is selected from the group consisting of an aliphatic alcohol having from 4 to 8 carbon atoms and a mixed solvent containing an aliphatic alcohol having from 4 to 8 carbon atoms.

3. The process as claimed in claim 1, wherein said solvent for the solution of the hydroxycyclobutenedione derivative is selected from the group consisting of dimethyl sulfoxide and dimethylformamide.

4. The process as claimed in claim 1, wherein said alcohol solvent of the solution of the aniline derivatives is selected from the group consisting of an aliphatic alcohol having from 4 to 8 carbon atoms and a mixed solvent of an aliphatic alcohol from 4 to 8 carbon atoms and an aromatic hydrocarbon.

5. The process as claimed in claim 1, wherein said reactoin is effected at a tempeature of from about 60° to about 140° C. for a period of from about 1 to about 50 hours.

6. The process as claimed in claim 1, wherein said dropwise additon is effected at a rate of from 0.01 to 10 mmol of the arylhydroxycyclobutenedione salt or hydroxycyclobutenedione derivative per minutes.

7. The process as claimed in claim 1, wherein said arylhydroxycyclobutenedione salt is a trialkylammonium salt.

8. The process as claimed in claim 1, wherein derivative comprising the aniline derivative, the alcohol solvent, and an acidic substrate selected from the group consisting of organic or inorganic acids.

9. The process as claimed in claim 8, wherein said acidic substance is present in an amount of from 1.1 to 3 equivalents to the arylhydroxycyclobutenedione salt.

10. The process as claimed in claim 8, wherein said acidic substance is sulfuric acid or oxalic acid.

11. The process as claimed in claim 1, wherein said alcohol solvent of the solution of the aniline derivative is an aliphatic alcohol having a boiling point of 130° C or higher, and the solution of the hydroxycyclobutenedione derivative is added dropwise to the solution of the aniline derivative in said solvent under reduced pressure of from 5 to 200 Torr.

* * * * *

UNITED STATES PATENT AND TRADEMARK OFFICE
CERTIFICATE OF CORRECTION

PATENT NO. : 5,041,665

DATED : August 20, 1991

INVENTOR(S) : Yutaka Akasaki et al.

It is certified that error appears in the above-identified patent and that said Letters Patent is hereby corrected as shown below:

Abstract, line 12, after "exhibits" change "and" to --high--.

Claim 1, column 29, line 61, change "R5 and R6" to --$R_5$, and $R_6$--.

Claim 1, column 29, line 64, change "R8" to --$R_8$--.

Claim 1, column 30, line 20, change "hydroxycyclobutendione" to --hydroxycyclobutenedione--.

Claim 1, column 30, line 40, change " 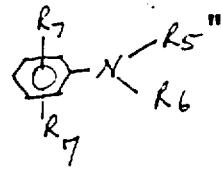 " to -- 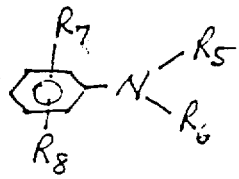 --.

Claim 5, column 30, line 64, change "reactoin" to --reaction--.

Claim 6, column 30, line 68, change "additon" to --addition--.

UNITED STATES PATENT AND TRADEMARK OFFICE
CERTIFICATE OF CORRECTION

PATENT NO. : 5,041,665

DATED : August 20, 1991

INVENTOR(S) : Yutaka Akasaki, et al.

It is certified that error appears in the above-identified patent and that said Letters Patent is hereby corrected as shown below:

Claim 8, column 31, line 9, after "wherein" insert --said solution of the arylhydroxycyclobutenedione salt is added dropwise to the alcohol solution of the aniline--.

Signed and Sealed this

Thirteenth Day of April, 1993

Attest:

STEPHEN G. KUNIN

*Attesting Officer*      *Acting Commissioner of Patents and Trademarks*